United States Patent
Mahar et al.

(10) Patent No.: US 9,922,171 B2
(45) Date of Patent: Mar. 20, 2018

(54) PHARMACEUTICAL ORDER VERIFICATION FOR AN AUTOMATED PHARMACY SYSTEM

(71) Applicant: Humana Inc., Louisville, KY (US)

(72) Inventors: Michael Mahar, Phoenix, AZ (US); Atin Kapadia, Chandler, AZ (US)

(73) Assignee: Humana Inc., Louisville, KY (US)

( * ) Notice: Subject to any disclaimer, the term of this patent is extended or adjusted under 35 U.S.C. 154(b) by 81 days.

(21) Appl. No.: 14/453,073

(22) Filed: Aug. 6, 2014

(65) Prior Publication Data

US 2016/0357939 A1    Dec. 8, 2016

Related U.S. Application Data

(60) Provisional application No. 61/862,921, filed on Aug. 6, 2013.

(51) Int. Cl.
*G07F 9/02* (2006.01)
*G06F 19/00* (2018.01)

(52) U.S. Cl.
CPC .......... *G06F 19/3462* (2013.01); *G07F 9/026* (2013.01)

(58) Field of Classification Search
CPC ............. G06F 19/3462; G06F 19/3456; G06F 17/0092; G06Q 50/22; G06Q 50/24
USPC ................................. 700/237, 240, 242–244
See application file for complete search history.

(56) References Cited

U.S. PATENT DOCUMENTS

| | | | |
|---|---|---|---|
| 5,597,995 A | 1/1997 | Williams et al. | |
| 5,907,493 A * | 5/1999 | Boyer | G06F 19/3462 700/213 |
| 8,231,749 B2 | 7/2012 | Dent et al. | |
| 8,467,897 B2 * | 6/2013 | Holmes | G06Q 20/40145 700/216 |
| 2004/0099683 A1 * | 5/2004 | Shows | G06F 19/3462 221/263 |
| 2006/0025884 A1 * | 2/2006 | Henkel | B65B 5/103 700/216 |
| 2006/0253346 A1 * | 11/2006 | Gomez | G06Q 30/02 705/28 |
| 2007/0043469 A1 * | 2/2007 | Draper | G06F 19/3462 700/231 |

(Continued)

*Primary Examiner* — Patrick Cicchino
(74) *Attorney, Agent, or Firm* — Standley Law Group LLP

(57) ABSTRACT

A pharmaceutical order verification system and method for an automated pharmacy system is disclosed. A computerized line control application controls a dispensing line, facilitates automated dispensing of drugs into vials, and collects and records data for dispensed drug as well as each verification step performed by a pharmacist. In an example embodiment, pharmacist verification occurs in connection with replenishing the drugs in automated tablet counters and in connection with verifying a specified percentage of orders for each automated tablet counter. During the replenishment process, the pharmacist verifies that a replenishment canister has been loaded with the correct drug in the appropriate dosage and strength. During the order verification step, a pharmacist verifies the contents of vial matches the prescription order data. The line control application tracks the number of orders that are identified for pharmacist verification to ensure verification requirements are met for each automated tablet counter.

12 Claims, 5 Drawing Sheets

(56) References Cited

U.S. PATENT DOCUMENTS

| | | | | |
|---|---|---|---|---|
| 2008/0288105 | A1* | 11/2008 | Mauger | G07F 11/62 700/231 |
| 2009/0287350 | A1* | 11/2009 | Johnson | G06F 19/3462 700/236 |
| 2010/0181334 | A1* | 7/2010 | Imai | B65B 5/103 221/1 |
| 2011/0015783 | A1* | 1/2011 | Shows | G06F 19/3462 700/237 |
| 2012/0310410 | A1* | 12/2012 | Adams | G07F 5/18 700/237 |
| 2013/0262138 | A1* | 10/2013 | Jaskela | G06Q 50/22 705/2 |
| 2014/0025545 | A1* | 1/2014 | Carson | G06Q 30/018 705/29 |
| 2015/0005934 | A1* | 1/2015 | Bell | G06F 19/3462 700/237 |
| 2015/0225101 | A1* | 8/2015 | Van Wijngaarden | B65B 57/20 53/443 |

\* cited by examiner

PHARMACEUTICAL ORDER VERIFICATION FOR AN AUTOMATED PHARMACY SYSTEM

CROSS-REFERENCE TO RELATED APPLICATIONS

This application claims priority to US Provisional Patent Application No. 61/862,921, titled PHARMACEUTICAL ORDER VERIFICATION FOR AN AUTOMATED PHARMACY SYSTEM and filed on Aug. 6, 2013, the contents of which are incorporated herein by reference.

BACKGROUND

Many health benefit plan providers and retail pharmacies now offer their clients the option of obtaining prescription drugs by mail. Mail order pharmacies ship prescription drugs to a client's home so the client is not required to visit a pharmacy and to fill a prescription in person. For clients with chronic conditions or other conditions that require maintenance drugs, a mail order prescription program is an attractive benefit because it is more convenient for the clients and typically less expensive than obtaining prescription drugs at a neighborhood pharmacy. For many drugs, clients have the option of purchasing a drug fill in a 60-day or even a 90-day supply at a lower cost than a 30-day supply.

Many mail order pharmacies use automated pharmacy systems and dispensing lines to process and ship a high volume of prescriptions on a daily basis. Depending upon how the technology is implemented and deployed within a mail order pharmacy, a substantial number of steps in the fulfillment process may be automated and the need for human intervention minimized. Mail order pharmacies operated in the US, like their neighborhood counterparts, must be licensed in a state and are subject to numerous rules and regulations established by the licensing state's board of pharmacy. One common requirement is that a pharmacy, whether a neighborhood pharmacy or a mail order pharmacy, must meet pharmacist verification requirements for certain prescriptions. Verification typically involves reviewing medication orders and overseeing the preparation and selection or packaging of medication doses according to the order to verify the right medication is delivered to the right patient.

For automated pharmacy systems, pharmacist verification involves manual steps that must be integrated into the automated fulfillment process. At a minimum, the pharmacist must verify the appropriate drugs are dispensed in the vials that are shipped to a patient. Although pharmacist verification is required as part of the fulfillment process, pharmacist involvement is not required in all aspects of the fulfillment process. In fact, pharmacist involvement in the fulfillment process beyond verification requirements contributes substantial labor costs that can reduce the cost-effectiveness of an automated pharmacy system. Therefore, there is a need for an automated pharmacy system with pharmaceutical order verification that meets verification requirements in an efficient and cost effective manner.

SUMMARY

The present disclosure is directed to a pharmaceutical order verification system and method for an automated pharmacy system. The disclosed pharmaceutical order verification system and method incorporates pharmacist verification steps into automated processing of orders and maintains compliance with verification regulations from an oversight board such as a state Board of Pharmacy. A computerized line control application that controls a dispensing line and facilitates automated dispensing of drugs collects and records data for each verification step performed by a pharmacist. The computerized line control application operates in conjunction with security and control procedures that minimize manual intervention in the fulfillment workflow thereby reducing the likelihood of introducing human errors.

In an example embodiment, pharmacist verification occurs at two points in the fulfillment process. During the fulfillment process, pharmacist verification occurs 1) in connection with replenishing the drug supply in automated tablet counters; and 2) in connection with verifying a specified percentage of orders for each automated tablet counter. Each verification step is supported by computerized technology to collect and record data during the verification step. Security and control measures in the fulfillment process minimize the opportunities for manual intervention following verification so that the possibility of human errors in dispensing the drugs is minimized.

During the replenishment process, the pharmacist verifies that a replenishment canister has been loaded with the correct drug in the appropriate dosage and strength. Additional controls ensure the replenished canister is mounted on the appropriate automated pill counter in the automated dispensing system. Following the replenishment process, the process of dispensing drugs into vials for each pharmaceutical order is fully automated. Each pharmacy order identifies the drugs that a specified patient should receive. Based on the drugs identified in an order, vials are directed to the appropriate automated tablet counter where they are filled with the quantity identified in the order and then automatically sealed. Processing is fully automated until filled, sealed vials reach a packaging station where they are automatically dropped into shipping envelopes. An operator adds printed documentation to each order envelope and seals the envelope for shipping to a patient.

During the order verification step, a pharmacist verifies the contents of a vial matches the prescription order data. After each vial is filled, an image of the vial contents is captured by an in-line camera. As the vial passes under the in-line camera, an image of the vial contents is archived with the prescription order data. A pharmacist accesses a pharmacist verification application to view vial images and verify the contents of a vial matches the prescription order data. Orders that pass the pharmacist's verification proceed to packaging station while orders that do not pass the pharmacist's verification are rerouted for exception. In an example embodiment, applicable verification regulations require pharmacist verification for a specified percentage of orders for each automated tablet counter. A control application tracks the number of orders that are identified for pharmacist verification to ensure the percentage requirements are met for each automated tablet counter.

DETAILED DESCRIPTION OF EXEMPLARY EMBODIMENT(S)

Figure 1:
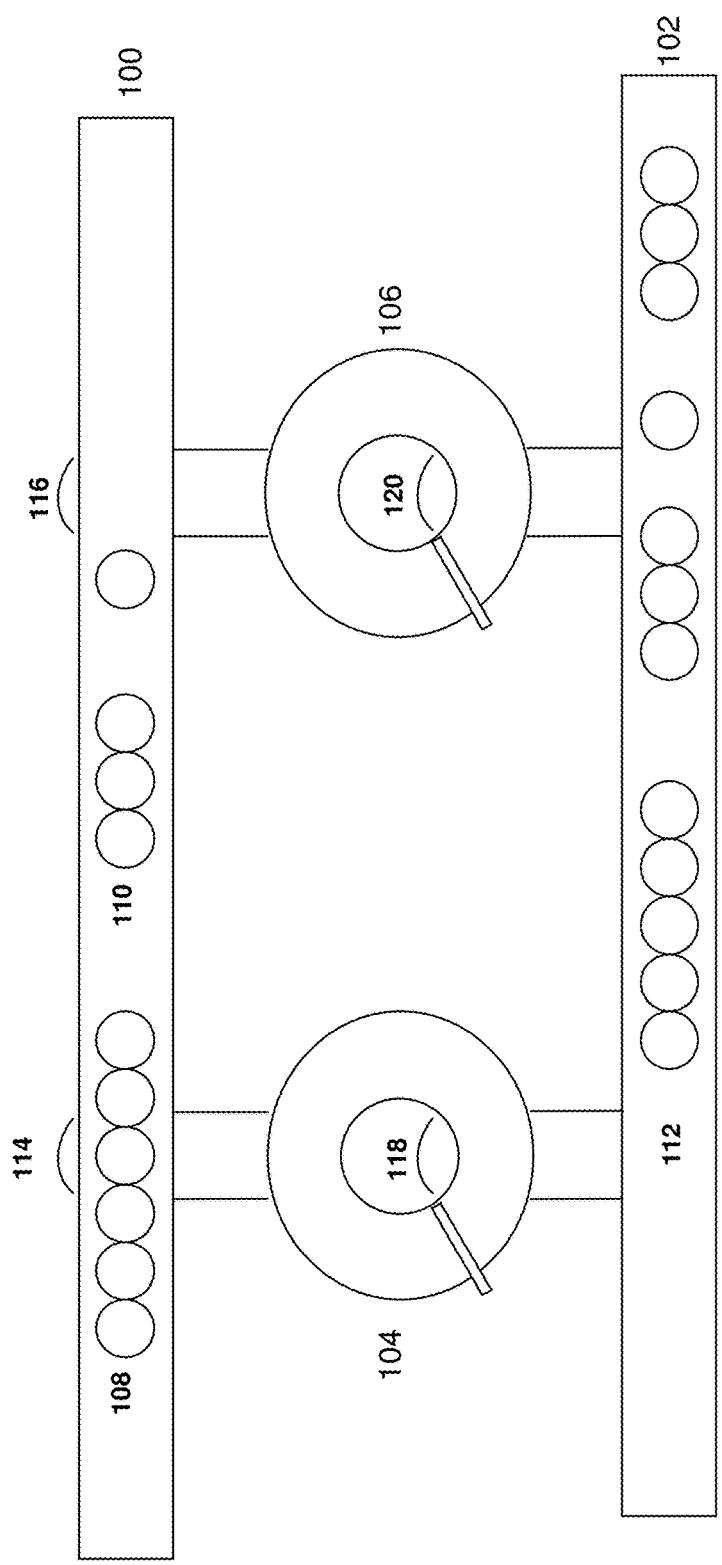
FIG. 1 is an automated dispensing line schematic diagram according to an example embodiment.

Referring to FIG. 1, an automated dispensing line schematic diagram according to an example embodiment is shown. The line may comprise a plurality of conveyors 100 102 for transporting vials 108 110 112 to automated tablet counters (ATC), sorting stations 104 106, and other locations on the line. In an example embodiment, each vial is transported in a puck that contains the vial and that comprises an RFID tag for use in routing the vial on the line and dispensing a medication from an ATC into the vial. A plurality of stations (ATCs, diverters, etc.) on the line comprise an RFID reader that reads the identifying information for a puck/vial and transmits it to a line control application that facilitates pharmaceutical order processing. The line control application receives order data (e.g., drug identifying data such as a National Drug Code (NDC), dosage, and quantity) as well as an RFID identifier for a puck that contains a vial in which the drug will be dispensed. Pucks are then routed by the line control application to appropriate stations (e.g., ATC with identified drug, sorting station, packaging station) so the drugs can be dispensed into the vials and shipped to patients. Vials are routed using the conveyors 100 102 and are diverted to various stations on the line or other conveyors using mechanical diverting devices 114 116 118 120 that "push" a vial from one direction of travel to another.

Figure 2:
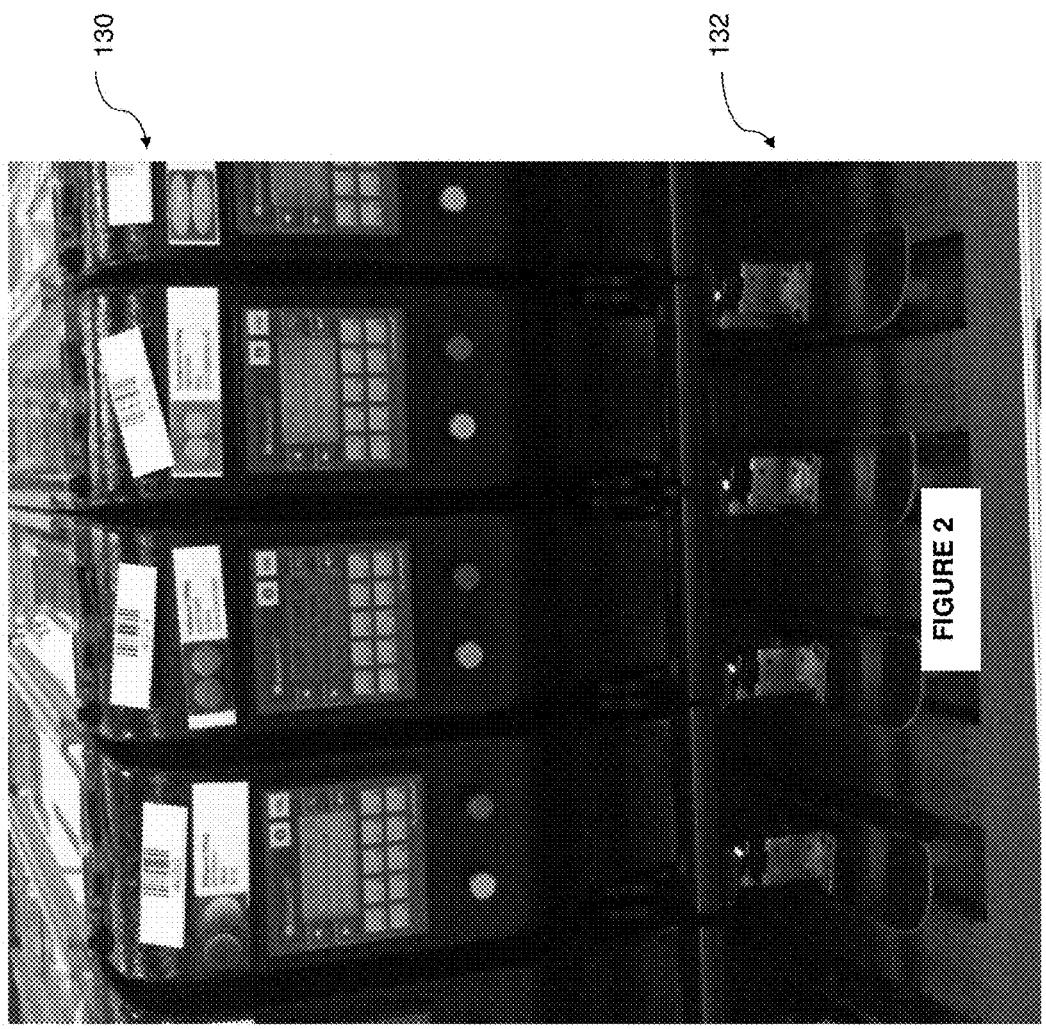
FIG. 2 is an ATC according to an example embodiment.

Referring to FIG. 2, an ATC according to an example embodiment is shown. In an example embodiment, an ATC is adapted to receive a canister containing the drug to be dispensed from the ATC. The canister is loaded at the top of the ATC 130 and the tablets or pills are dispensed through an opening at the bottom of the ATC 132. Each canister comprises a barcode that identifies the ATC location and contents. The ATCs also comprise various sensors and other components to track the dispensing of tablets or pills from the ATC. Data related to the dispensing of drugs is collected at each ATC and communicated to the line control application to facilitate the replenishment of ATCs when they become empty or nearly empty. While most of the fulfillment process is automated, replenishment of ATCs involves several manual steps. Data regarding the replenishment process is collected and recorded according to well-defined procedural controls, including pharmacist verification, to reduce the likelihood that the wrong drug is dispensed from an ATC.

Replenishment requests are processed through the line control application and routed to pharmacy associates that are responsible for loading ATC canisters and staging them for pharmacist review and verification. When an ATC on the dispensing line needs to be replenished, the replenishment request data (e.g., ATC identifier, ATC location, NDC) is added to a queue of requests. The pharmacist associate opens the request at a workstation, reviews the request, obtains the requested drug and fills the canister, and updates the request to indicate the canister has been filled. The request status is updated to indicate the canister is ready for pharmacist verification.

Figure 3:
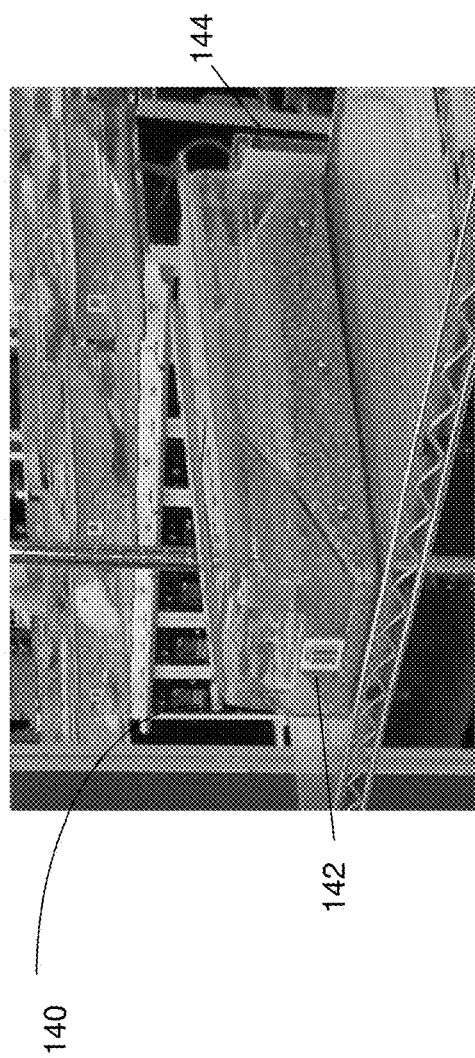
FIG. 3 is a replenishment canister for an ATC according to an example embodiment.

Referring to FIG. 3, a replenishment canister for an ATC according to an example embodiment is shown. A canister 140 is transparent to facilitate viewing of the canister contents. Each canister comprisesa bar code 142 that is associated with a description of the canister and its contents (e.g., NDC and dose). For example, one canister may be used to dispense CRESTOR® 10 mg tablets while another canister is used to dispense Celebrex® 200 mg tablets. Once a canister has been filled, the associate locks the canister with a cable tie 144 that also has a security tag barcode.

Figure 4:
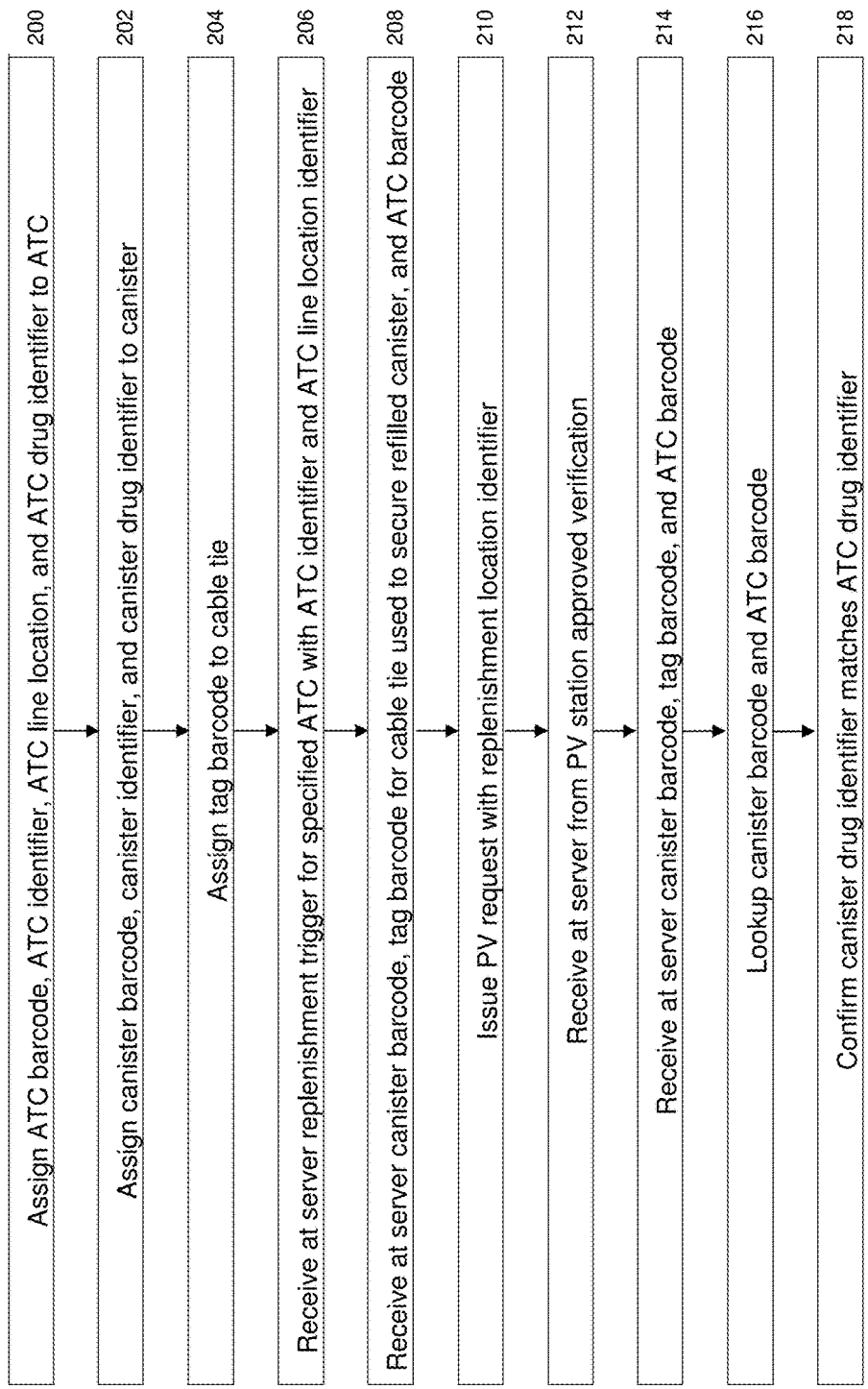
FIG. 4 is a flowchart for a secure replenishment software module according to an example embodiment.

Referring to FIG. 4, a flowchart for a secure replenishment software module according to an example embodiment is shown. Initially, identifying data such as barcodes for ATCs, canisters, and cable ties is entered in the module 200, 202, 204. A replenishment request comprising ATC identifying information is received at the module from the line control application 206. After a pharmacy associate fills a canister, the associate scans the canister barcode, security tag barcode for a cable tie used to secure the refilled canister, and ATC barcode and stages the canister for pharmacist review 208. The replenishment request is updated with the scanned data to indicate the canister is ready for pharmacist verification. A notification is sent to a pharmacist verification software module that alerts a pharmacist of the need to verify the canister contents 210.

The pharmacist completes the review of the replenishment canister at a pharmacist verification station. In an example embodiment, the request data is displayed for the pharmacist as well as an image of the requested drug. Once the pharmacist verifies the requested drug has been added to the canister, the replenishment request is updated with the verification data 212.

Following pharmacist verification, the canister is staged for loading on the ATC associated with the request. A pharmacy associate takes the canister to the ATC on the dispensing line, scans the canister barcode, loads the canister on the ATC, scans the ATC barcode, and scans the security tag (i.e., cable tie) barcode 214. The line control application receives the barcode data, performs a look up on the barcode data 216, and confirms the pharmacist-verified canister has been loaded on the appropriate ATC 218.

Once verified by a pharmacist, a change to the contents of a canister requires a breach of container, whether accidental or unintentional. As long as the pharmacist-verified canister remains intact during transport to the dispensing line and is loaded on the correct ATC, the ATC dispenses the appropriate drug. After an ATC has been replenished, the tablets or pills are automatically dispensed into vials and the vials are routed on the dispensing line for packaging. Filled vials automatically drop into labeled packages that are then sealed. As a result, in normal operation, no human contact or intervention with vials occurs after they have been filled from pharmacist-verified canisters.

In addition to verifying the contents of ATC replenishment canisters, pharmacists verify a specified percentage of orders for each ATC. In an example embodiment, a series of orders (e.g., specified number of orders following replenishment) are selected for pharmacist verification. Additionally, orders may be selected at random for pharmacist verification to ensure an appropriate number of orders are verified to meet verification requirements. For every ATC, a "Send to PV Frequency" parameter is configured. The parameter is based on the percentage of orders that are verified to meet state regulations or guidelines such as requirements from a state Board of Pharmacy.

Pharmacist verification is performed by capturing and displaying at a workstation the verification data that the pharmacist needs to review and verify a prescription order. The verification data includes prescribed drug data from the order (e.g., drug name, strength, dosage form, and quantity prescribed) and a digital image of a drug dispensed into a vial for shipment to the patient. The digital images are acquired from digital camera systems that are integrated into the automated dispensing line. During the fulfillment process, a digital image of every filled vial is captured and stored with the order data. The pharmacist reviews the prescription order data and image of the vial contents shown at the workstation to confirm the proper drug has been added to the vial to be dispensed to the patient.

Figure 5:
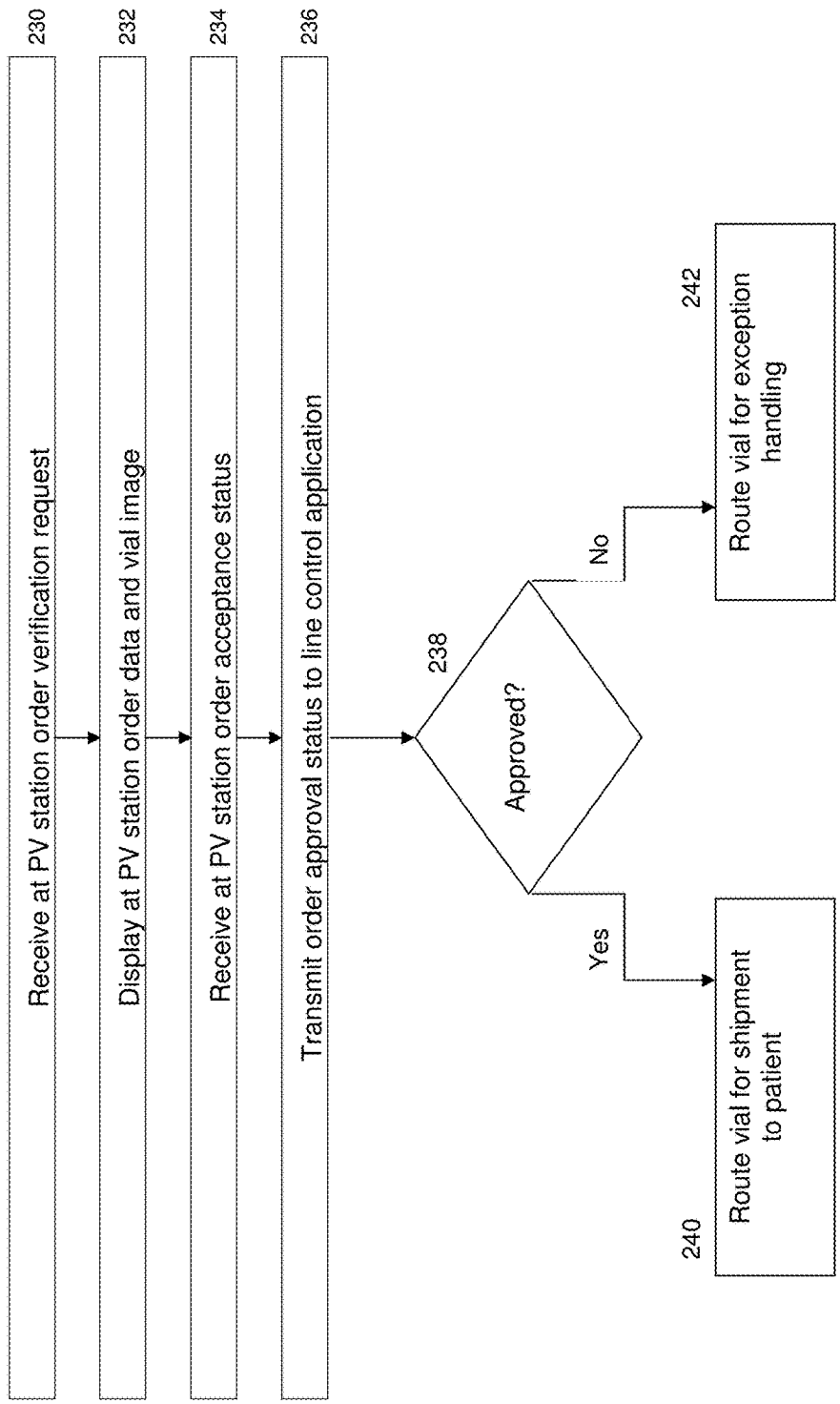
FIG. 5 is a flowchart of a pharmacist verification software module according to an example embodiment.

Referring to FIG. 5, a flowchart of a pharmacist verification software module according to an example embodiment is shown. The pharmacist receives the verification requests 230 and displays the order data and vial image 232. The pharmacist completes the review and submits an order acceptance indicator 234. The order approval status is transmitted to the line control application 236. If the order is approved 238, the vial is routed for shipment to the patient 240. If the order is not approved 238, the vial is routed for exception handling 242.

Vials that are not subject to pharmacist verification are "auto-verified" by the line control application. When a puck is auto-verified, the line control application determines the pharmacist identifier that performed the canister replenishment verification for the Active NDC, Active Lot Number, and Active Canister Identifier. The pharmacist identifier is then associated with the puck/vial and therefore, the order data. The item is also flagged as "auto-verified" in the system database. When a drug is dispensed from an ATC into a vial successfully, the line control application marks the puck/vial as verified unless one of the following conditions is met:

TABLE 1

| Auto-Verify Failure Conditions | |
| --- | --- |
| Sensor mismatch or allowable over/under count occurred. | Puck/vial routed to PV station; pharmacist verifies quantity. |
| Randomly generated number for order falls within configured "Send to PV Frequency" for ATC. | Puck/vial routed to PV station. |
| Puck is one of first "Number of Pucks to PV After Replenishment" system parameter after replenishment of ATC. (e.g., if 1,000 pills are left in the old canister when replenishment occurred, then after those 1,000 pills are dispensed, require manual pharmacist verification of the next N pucks/vials to dispense from that ATC. | Puck/vial routed to PV station. System flags single orders or puck/vials already flagged to go to a tote line for PV (less invasive to the depucker). If a "Max ATC PV Skips" number of puck/vials do not qualify according to this logic (i.e., requisite number of puck/vials have not been routed to manual PV), send the next puck/vials to manual PV regardless of their nature until the requisite number of pucks have been sent. |
| Order includes a "manual pick puck" item. | Puck is routed to a separate "tote line" for PV. When a puck is flagged for tote line PV, all pucks in that order are flagged for routing to the tote line; pharmacist verifies only vials that were not auto-verified. |

Vials that are auto-verified are also imaged during the dispensing process so that an image of the vial contents can be archived with the order. If the need arises after the order has been filled, the vial contents can be verified using the order data and archived image.

The disclosed pharmaceutical order verification system and method comprises a computerized line control application that operates in conjunction with security and control procedures to maximize the likelihood the correct drug is dispensed from an ATC. Pharmacist verification occurs in connection with replenishing the drugs in ATCs and in connection with verifying a specified percentage of orders for each ATC. Each verification step is supported by computerized technology to collect and record data during the verification step. While certain embodiments of the present invention are described in detail above, the scope of the invention is not to be considered limited by such disclosure, and modifications are possible without departing from the spirit of the invention as evidenced by the following claims:

What is claimed is:

1. A computerized method for processing vials on an automated dispensing line comprising:
   (a) assigning at a server to an automated tablet counter (ATC) identifier:
      (1) an ATC barcode; and
      (2) drug identifying data for a drug dispensed from said ATC said drug identifying data comprises a drug code and a drug dosage;
   (b) assigning at said server to a drug canister identifier a drug canister barcode;
   (c) assigning at said server to a canister security tag a security tag barcode;
   (d) receiving at said server a replenishment request comprising said ATC identifier;
   (e) transmitting a notification to a pharmacist requesting the pharmacist to verify the contents of the drug canister associated with the drug canister identifier:
      (1) displaying the notification to the pharmacist requesting the pharmacist to verify the contents of the drug canister on a pharmacist verification software module; and
      (2) displaying an image of a drug associated with the drug canister;
   (f) receiving at said server a pharmacist verification approval for said replenishment request confirming contents of said drug canister matches said drug identifying data;
   (g) receiving at said server barcode scan data for a scanned ATC, a scanned drug canister, and a scanned security tag;
   (h) confirming at said server said barcode scan data matches said ATC barcode, said drug canister barcode, and said security tag barcode;
   (i) receiving at said server filled prescription order data for a plurality of vials filled at said ATC;
   (j) transmitting a request to verify said order data and vial contents to a pharmacist, said request comprising filled prescription order data and an image of the contents of at least one of said plurality of vials; and (k) receiving at said server pharmacist order verification status for a specified number of said plurality of vials.

2. The computerized method of claim 1 wherein said security tag barcode is a barcode for a cable tie.

3. The computerized method of claim 1 wherein said specified number of said plurality of vials is a percentage of said plurality of vials.

4. The computerized method of claim 1 wherein said specified number of said plurality of vials is a specified number of vials following replenishment.

5. The computerized method of claim 1 wherein said replenishment request further comprises an ATC location on a dispensing line.

6. The computerized method of claim 1 further comprising:
   (l) routing said specified number of said plurality of vials according to said order approval status.

7. The computerized method of claim 6 further comprising:
   (m) if said order approval status is approved, routing said vial for shipment; and
   (n) if said order approval status is not approved, routing said vial for exception handling.

8. A computerized system for processing vials on an automated dispensing line comprising:
   (a) a server executing programming instructions to:
      (1) assign at said server to an automated tablet counter (ATC) identifier:
         (i) an ATC barcode; and
         (ii) drug identifying data for a drug dispensed from said ATC, said drug identifying data comprises a drug code and a drug dosage;
      (2) assign at said server to a drug canister identifier a drug canister barcode;
      (3) assign at said server to a canister security tag a security tag barcode;
      (4) receive at said server a replenishment request comprising said ATC identifier;
      (5) transmit from said server a notification requesting a pharmacist to verify the contents of a drug canister associated with a drug canister identifier;
      (6) receive at said server a pharmacist verification approval for said replenishment request confirming contents of said drug canister matches said drug identifying data;
      (7) receive at said server barcode scan data for a scanned ATC, a scanned drug canister, and a scanned security tag;
      (8) confirm at said server said barcode scan data matches said ATC barcode, said drug canister barcode, and said security tag barcode;
      (9) receive at said server filled prescription order data for a plurality of vials filled at said ATC;
      (10) receive at said server pharmacist verification order approval status for a specified number of said plurality of vials;
      (11) route said vial for shipment if said order approval status is approved; and
      (12) route said vial for exception handling if said order approval status is not approved;
   (b) a pharmacist verification station executing programming instructions to:
      (1) display a replenishment confirmation request for said drug canister and display an image of a drug associated with the drug canister;
      (2) receive and transmit to said server said pharmacist verification approval for said replenishment request confirming contents of said drug canister matches said drug identifying data;
      (3) receive a pharmacist verification request to approve a plurality of vial contents where such verification request includes an image of contents of at least one of said plurality of vials;
      (4) display pharmacist verification approval requests for said specified number of said plurality of vials where said displayed approval request comprises the image of at least on of said plurality of vials; and
      (5) receive and transmit to said server pharmacist verification order approval status for said specified number of said plurality of vials.

9. The computerized system of claim 8 wherein said security tag barcode is a barcode for a cable tie.

10. The computerized system of claim 8 wherein said specified number of said plurality of vials is a percentage of said plurality of vials.

11. The computerized system of claim 8 wherein said specified number of said plurality of vials is a specified number of vials following replenishment.

12. The computerized system of claim 8 wherein said replenishment request further comprises an ATC location on a dispensing line.

* * * * *